(12) United States Patent
Hommeltoft

(10) Patent No.: US 8,319,001 B2
(45) Date of Patent: Nov. 27, 2012

(54) PROCESS FOR REACTING ISO-ALKANE TO MAKE NAPHTHA AND MIDDLE DISTILLATE

(75) Inventor: Sven Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 13/537,667

(22) Filed: Jun. 29, 2012

(65) Prior Publication Data

US 2012/0271086 A1 Oct. 25, 2012

Related U.S. Application Data

(62) Division of application No. 12/628,009, filed on Nov. 30, 2009.

(51) Int. Cl.
*C07C 2/56* (2006.01)
*C07C 2/06* (2006.01)
(52) U.S. Cl. ......... 585/331; 585/332; 585/521; 585/709
(58) Field of Classification Search .................. 585/331, 585/332, 521, 709
See application file for complete search history.

(56) References Cited

U.S. PATENT DOCUMENTS

| | | |
|---|---|---|
| 6,849,773 B2 | 2/2005 | Podrebarac et al. |
| 6,919,016 B2 | 7/2005 | Podrebarac et al. |
| 7,432,409 B2 | 10/2008 | Elomari et al. |
| 7,449,612 B2 | 11/2008 | Smith et al. |
| 7,531,707 B2 | 5/2009 | Harris et al. |
| 7,566,799 B2 | 7/2009 | Steinbrenner et al. |
| 7,569,740 B2 | 8/2009 | Elomari |
| 7,601,861 B2 | 10/2009 | Bottke et al. |
| 7,919,663 B2 | 4/2011 | Hommeltoft et al. |
| 7,919,664 B2 | 4/2011 | Hommeltoft et al. |
| 7,923,593 B2 | 4/2011 | Hommeltoft |
| 7,955,495 B2 | 6/2011 | Hommeltoft et al. |
| 2008/0045763 A1 | 2/2008 | Cross et al. |
| 2008/0146858 A1 | 6/2008 | Elomari et al. |
| 2009/0192339 A1 | 7/2009 | Timken et al. |

FOREIGN PATENT DOCUMENTS

EP 1868968 A2 12/2009

OTHER PUBLICATIONS

CDTECH, 2006 Q&A and Technology Forum slide, NPRA, Q#30.

*Primary Examiner* — Thuan D Dang
(74) *Attorney, Agent, or Firm* — Susan M. Abernathy

(57) ABSTRACT

A process for reacting an iso-pentane, comprising:
a) partially converting an olefinic feedstock comprising at least 15 wt % iso-pentene to make a converted olefinic feedstock, wherein the iso-pentene is reduced and an amount of 2-pentene is retained; and
b) alkylating the iso-pentane with the converted olefinic feedstock to make a naphtha and a middle distillate.

10 Claims, 1 Drawing Sheet

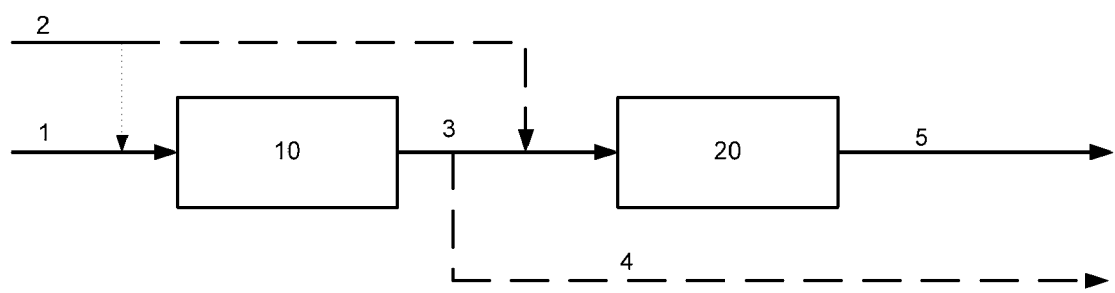

PROCESS FOR REACTING ISO-ALKANE TO MAKE NAPHTHA AND MIDDLE DISTILLATE

This application is a divisional of U.S. patent application Ser. No. 12/628,009, filed Nov. 30, 2009, in Group Art Unit 1772; and herein incorporated in its entirety. This application also claims priority to U.S. patent application Ser. No. 12/628,020, filed Nov. 30, 2009; also herein incorporated in its entirety.

This application is related to a co-filed application, titled "ALKYLATING ISO-PENTANE WITH A CONVERTED OLEFINIC FEEDSTOCK;" herein incorporated in its entirety.

TECHNICAL FIELD

This invention is directed to processes for reacting iso-pentane to make alkylate products.

SUMMARY

This invention provides a process for reacting an iso-pentane with an olefinic feedstock, comprising: a) partially converting one or more olefins in the olefinic feedstock with an ionic liquid catalyst to make a converted olefinic feedstock, wherein one or more linear internal olefins in the converted olefinic feedstock remain unconverted; and b) alkylating the converted olefinic feedstock with the iso-pentane to make one or more alkylate products.

This invention also provides a process for reacting an iso-pentane, comprising: alkylating the iso-pentane with a converted olefinic feedstock comprising at least 5 wt % C5 olefins, wherein the C5 olefins in the converted olefinic feedstock are predominantly 2-pentene, to make a naphtha and a middle distillate, and wherein a formation of iso-butane during the alkylating is less than 35 wt % of an amount of olefins in the converted olefin feedstock.

This invention also provides a process for reacting an iso-pentane, comprising: a) partially converting an olefinic feedstock comprising at least 15 wt % iso-pentene to make a converted olefinic feedstock, wherein the iso-pentene is reduced and an amount of 2-pentene is retained; and b) alkylating the iso-pentane with the converted olefinic feedstock to make a naphtha and a middle distillate.

BRIEF DESCRIPTION OF THE DRAWING

FIG. 1 is a process flow diagram of an embodiment of the invention

DETAILED DESCRIPTION

The partially converting reduces undesired components in the olefinic feedstock, while one or more linear internal olefins remain unconverted. For example, the partially converting may convert one or more iso-olefins, one or more alpha-olefins, or a mixture thereof. In other embodiments the partially converting may reduce one or more of dienes, mercaptans, nitrogen & sulphur containing hydrocarbons, alpha-olefins and iso-olefins.

In one embodiment, the process for partially converting is different from olefin isomerization. Examples of processes that are useful for partially converting are dimerization, trimerization, oligomerization, metathesis, and catalytic distillation.

The olefinic feedstock can be any olefinic feedstock comprising undesired components that can be removed by the partially converting step, as well as comprising one or more linear internal olefins. The undesired components, for example, can be iso-olefins, alpha-olefins, dienes, or mercaptans. In one embodiment, the olefinic feedstock comprises one or more iso-olefins, one or more alpha-olefins, or a mixture thereof. For example, the olefinic feedstock may comprise a mixture of C5 olefins.

In one embodiment, the olefinic feedstock comprises at least 15 wt % iso-pentene. The olefinic feedstock can have, for example at least 18 wt %, at least 20 wt %, at least 25 wt %, or at least 30 wt % iso-pentene.

In one embodiment, the olefinic feedstock may be from a FCC unit or a coker unit. In other embodiments, the olefinic feed may be from a wax cracker, such as an autothermal cracking reactor. Olefins are typically produced in petroleum refineries using either the FCC process, the delayed coking process, or less often the fluidized coking process. In the future, as more waxy feeds become available from new sources (such as from Fischer-Tropsch processes such as Gas-to-Liquid, Coal-to-Liquid, or Biomass-to-Liquid), wax crackers will become more economic. FCC units use a fluidized catalyst system to facilitate catalyst and heat transfer between a reactor and a regenerator. Combustion of coke in the regenerator provides the heat necessary for the reactor. A good overview of examples of FCC units are described in "UOP Fluid Catalytic Cracking (FCC) and Related Processes", UOP 4523-7, June 2008; herein incorporated in its entirety.

A delayed or fluidized coker is an oil refinery processing unit that converts the residual oil from a vacuum distillation column or an atmospheric distillation column into low molecular weight hydrocarbon gases, naphtha, light and heavy gas oils, and petroleum coke. The process thermally cracks the long chain hydrocarbon molecules in the residual oil feed into shorter chain molecules. The coke from a coker can either be fuel grade (high in sulphur and metals) or anode grade (low in sulphur and metals).

The shorter chain molecules produced in a coker are richer in alpha olefin content than olefin feeds from a FCC unit. The high alpha olefin content in the shorter chain molecules produced in a coker unit form because cokers crack primarily by electron-promoted free radical mechanisms, whereas a FCC unit cracks by proton-promoted acid mechanisms. The shorter chain molecules from a coker also have a relatively high concentration of olefins. The higher the normal-paraffin content in the feed to the coker unit, the greater the alpha olefin content of the shorter chain molecules produced in the coker unit.

In one embodiment the coker unit is a delayed coker unit. A delayed coker unit is a type of coker unit whose process consists of heating a residual oil feed to its thermal cracking temperature in a furnace with multiple parallel passes. This cracks the heavy, long chain hydrocarbon molecules of the residual oil into coker gas oil and petroleum coke.

Delayed coker units may provide a higher content of alpha olefins than feeds from a FCC unit. The content of the alpha olefins is dependent on the normal-paraffin content in the feed to the delayed coker unit. Many oil refineries have delayed coker units and the shorter chain molecules produced in the delayed coker units are not in as high demand for conventional sulfuric or HF alkylation plants or for chemicals, so their availability and pricing are favorable.

The partially converting can be done with an ionic liquid catalyst. The ionic liquid catalyst is composed of at least two components which form a complex. The ionic liquid catalyst comprises a first component and a second component. The first component of the ionic liquid catalyst may comprise a Lewis Acid selected from components such as Lewis Acid compounds of Group 13 metals, including aluminum halides, alkyl aluminum halide, gallium halide, and alkyl gallium halide (see International Union of Pure and Applied Chemistry (IUPAC), version 3, October 2005, for Group 13 metals of the periodic table). Other Lewis Acidic compounds besides those of Group 13 metals may also be used. In one embodiment the first component is aluminum halide or alkyl aluminum halide. For example, aluminum trichloride can be the first component of the ionic liquid catalyst.

The second component making up the ionic liquid catalyst is an organic salt or mixture of salts. These salts may be characterized by the general formula Q+A−, wherein Q+ is an ammonium, phosphonium, boronium, iodonium, or sulfonium cation and A− is a negatively charged ion such as Cl−, Br−, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$, $SO_3CF_3^-$, and 3-sulfurtrioxyphenyl. In one embodiment the second component is selected from those having quaternary ammonium halides containing one or more alkyl moieties having from about 1 to about 12 carbon atoms, such as, for example, trimethylamine hydrochloride, methyltributylammonium halide, or substituted heterocyclic ammonium halide compounds, such as hydrocarbyl substituted pyridinium halide compounds for example 1-butylpyridinium halide, benzylpyridinium halide, or hydrocarbyl substituted imidazolium halides, such as for example, 1-ethyl-3-methyl-imidazolium chloride.

In one embodiment the acidic ionic liquid catalyst is selected from the group consisting of hydrocarbyl substituted pyridinium chloroaluminate, hydrocarbyl substituted imidazolium chloroaluminate, and mixtures thereof. For example, the acidic ionic liquid catalyst can be an acidic haloaluminate ionic liquid, such as an alkyl substituted pyridinium chloroaluminate or an alkyl substituted imidazolium chloroaluminate of the general formulas A and B, respectively.

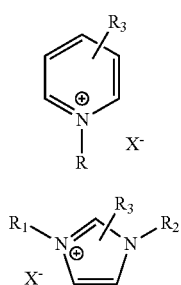

In the formulas A and B; R, $R_1$, $R_2$, and $R_3$ are H, methyl, ethyl, propyl, butyl, pentyl or hexyl group, X is a chloroaluminate. In the formulas A and B, R, $R_1$, $R_2$, and $R_3$ may or may not be the same.

In another embodiment the acidic ionic liquid catalyst can have the general formula RR′R″ $NH^+Al_2Cl_7^-$, wherein N is a nitrogen containing group, and wherein RR′ and R″ are alkyl groups containing 1 to 12 carbons, and where RR′ and R″ may or may not be the same.

The presence of the first component should give the ionic liquid a Lewis or Franklin acidic character. Generally, the greater the mole ratio of the first component to the second component, the greater is the acidity of the ionic liquid catalyst.

The ionic liquid catalyst may be either supported or unsupported. The term "supported" means that the catalyst is dispersed on a second material that enhances the effectiveness or minimizes the cost of the catalyst. Sometimes the support is merely a surface upon which the catalyst is spread to increase the surface area. In some embodiments, the support only gives a physical promotion and does not chemically interact with the ionic liquid other than making sure that the ionic liquid wets the surface of the support. In other embodiments, the ionic liquid and the support may also interact in a way that affects the catalytic reaction. Examples of supports that may be used include carbonaceous solids, silicaceous solids, polymers, inorganic oxides, and strongly acidic ion exchange resins.

In one embodiment, the ionic liquid catalyst is mixed with a hydrogen halide or an alkyl halide. The hydrogen halide or alkyl halide can boost the overall acidity and change the selectivity of the ionic liquid catalyst. It is believed that the alkyl halide decomposes under hydroconversion conditions to liberate Bronsted acids or hydrogen halides, such as hydrochloric acid (HCl) or hydrobromic acid (HBr). These Bronsted acids or hydrogen halides promote the alkylation reaction. Examples of alkyl halides are alkyl chloride, alkyl bromide, alkyl iodide, alkyl fluoride, and mixtures thereof. In one embodiment the alkyl halide is selected from the group consisting of alkyl chloride, alkyl bromide, alkyl iodide, and mixtures thereof. In one embodiment the halide in the hydrogen halide or alkyl halide is the same as a halide component of the acidic ionic liquid catalyst. In one embodiment the alkyl halide is an alkyl chloride. A hydrogen chloride or an alkyl chloride may be used advantageously, for example, when the acidic ionic liquid catalyst is a chloroaluminate.

In one embodiment, the formation of iso-butane during the alkylating step is reduced compared to a process not including the partially converting step. Iso-butane is sometimes a less desired product than other heavier alkylates. The formation of iso-butane during the alkylating is generally less than 40 wt % of an amount of olefins in the converted olefinic feedstock. In other embodiments, the formation of iso-butane can be less than 35 wt %, less than 30 wt %, less than 25 wt %, less than 20 wt %, or even less than 10 wt % of an amount of olefins in the converted olefinic feedstock. In one embodiment, the formation of iso-butane during the alkylating is less than 15 wt %, or less than 10 wt % of an amount of olefins in the converted olefinic feedstock.

In one aspect, the one or more products made during the alkylating step comprise one or more of light naphtha, heavy naphtha, and jet fuel.

A "naphtha" is a lighter hydrocarbon product having a boiling range between 100° F. to 400° F. (38° C. to 204° C.). A light naphtha has a lower boiling range than a heavy naphtha. In the context of this disclosure, light naphtha is exemplified by hydrocarbons having boiling points in the range of 40-130° C., heavy naphtha is exemplified by hydrocarbons having boiling points in the range of 130-200° C., jet fuel is exemplified by hydrocarbons having boiling points in the range of 200-290° C., diesel fuel is exemplified by hydrocarbons having boiling points in the range of 290-360° C., light oil is exemplified by hydrocarbons having boiling points in the range of 316° C. and higher, and heavy oil is exemplified by hydrocarbons having a boiling point in the range of 360- about 550° C.

A "middle distillate" is a hydrocarbon product having a boiling range between 250° F. to 1100° F. (121° C. to 593° C.). The term "middle distillate" includes the diesel, heating oil, jet fuel, and kerosene boiling range fractions. It may also include a portion of naphtha or light oil. A "jet fuel" is a hydrocarbon product having a boiling range in the jet fuel boiling range. The term "jet fuel boiling range" refers to hydrocarbons having a boiling range between 280° F. and 572° F. (138° C. and 300° C.).

In one embodiment, the process for reacting an iso-pentane comprises alkylating the iso-pentane with a converted olefinic feedstock comprising at least 5 wt % C5 olefins, wherein the C5 olefins are predominantly 2-pentene. By predominantly, it is meant that greater than 50 wt % of the C5 olefins in the converted olefinic feedstock are 2-pentene. In some embodiments, the C5 olefins are greater than 60, 70, 75, 80, 90, or 95 wt % 2-pentene in the converted olefinic feedstock. In one embodiment, the C5 olefins in the converted olefinic feedstock are at least 90 wt % 2-pentene.

The converted olefinic feedstock comprises one or more linear internal olefins. In one embodiment the converted olefinic feedstock comprises at least 5, at least 8, or at least 10 wt % C5 olefins.

In one embodiment the converted olefinic feedstock has been partially converted prior to the alkylating to reduce the level of an iso-olefin, an alpha-olefin, or a mixture thereof. In another embodiment the converted olefinic feedstock is one that is selected or blended to contain C5 olefins that are predominantly 2-pentene.

The alkylating is done in the presence of an acidic catalyst. In one embodiment the alkylating is done in the presence of an ionic liquid catalyst. Examples of processes for alkylating olefinic feedstocks comprising pentene with iso-pentane in the presence of an ionic liquid catalyst to make one or more alkylate products are described in U.S.20090192339A1, U.S.20090171133A1, U.S.20090171134A1, U.S.20090166257A1, U.S.20090107032A1, U.S.20080146858A1, and U.S.20060131209A1.

In one embodiment, the partially converting and alkylating are done in the presence of one or more ionic liquid catalysts. The one or more ionic liquid catalysts can either be the same or be different during the partially converting and alkylating. In one embodiment, the one or more ionic liquid catalysts comprise a butyl-pyridinium chloroaluminate.

The following is a description of an embodiment of the invention with reference to FIG. 1:

An olefinic feedstock (1) is partially converted in a reactor (10) to form an effluent (3) comprising one or more linear internal olefins. An iso-alkane (2) may be optionally added to either the olefinic feedstock (1) or to the effluent (3). The effluent (3) is fed to an alkylation reactor (20) wherein the one or more linear internal olefins are alkylated to produce alkylate products (5). Products contained in the effluent (3) may be optionally isolated and withdrawn (4) before the effluent (3) is fed to the alkylation reactor (20). In one embodiment the olefinic feedstock comprises iso-pentene, alpha-pentene, or a mixture thereof. In one embodiment the iso-alkane is iso-pentane. In one embodiment the one or more linear internal olefins comprises 2-pentene.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

EXAMPLES

Example 1

Iso-pentane was reacted with mixed FCC pentenes in the presence of N-butyl-pyridinium heptachlorodialuminate and HCl in a 100 ml continuously stirred tank reactor (CSTR) running at 1600 RPM at a temperature of 10° C. and 100 psi pressure. The iso-pentane was a refinery grade mixture comprising 76 wt % iso-pentane, 15 wt % n-pentane, 7 wt % n-butane, 2 wt % iso-hexanes and 1 wt % hydrocarbons lighter than n-butane.

The mixed FCC pentenes were withdrawn at a refinery and had the composition as shown in Table 1:

TABLE 1

| Composition of refinery FCC pentene mixture | |
| --- | --- |
| Component | Wt % |
| n-Butane | 2 |
| Butenes (mostly 2-butene) | 7 |
| i-Pentane | 44 |
| n-Pentane | 6 |
| 1-Pentene | 1 |
| 2-Pentene | 16 |
| i-Pentenes | 20 |
| C6+ | 4 |

The iso-pentane stream (325 g/hr) was mixed with the mixed pentene stream (113 g/hr) and fed to the alkylation reactor together with N-butyl-pyridinium ionic liquid (60 g/hr) and HCl (approx. 0.8 g/hr). The effluent from the reactor was depressurized, the ionic liquid separated out, and the products fractionated. The volumetric mass balance showed that one kg olefin reacted with 1.93 kg iso-pentane to yield 0.68 kg iso-butane, 1.03 kg light naphtha (bp: 40-130° C.), 0.85 kg heavy naphtha (bp: 130-175° C.), 0.33 kg jet fuel (bp: 175-260° C.) and 0.04 kg heavier products (>260° C.)

Example 2

The same equipment and feeds as described in Example 1 were used in this experiment. The mixed pentenes were introduced into the CSTR at a rate of 105 g/hr and the ionic liquid at a rate of 60 g/hr. The HCl flow was varied in the range of 0.10-0.41 g/hr and the iso-pentane was fed at either of 293 g/hr or 146 g/hr during the course of the experiment. Though the lower iso-pentane feed rate appeared to give higher olefin conversion it did not seem to have a significant effect on the C6+ product composition. The reaction was conducted at 10° C. and 100 psi. The product was withdrawn as described in Example 1. The volumetric mass balance showed that 1 kg converted olefin yielded 0.21 kg light naphtha (bp 40-130° C.), 0.27 kg heavy naphtha (bp: 130-175° C.), 0.27 kg jet fuel (bp: 175-260° C.) and 0.25 kg heavier material (bp>260° C.). No iso-pentane was consumed and no iso-butane was produced. The unconverted olefin was predominantly 2-pentene which typically constituted more than 80% of the C5 olefins in the product.

Example 3

A premixed feed, modeling the products from a partial conversion process similar to that described in Example 2, contained 10 wt % 2-pentene, 89 wt % iso-pentane and 1 wt % n-pentane. The premixed feed was fed to the 100 ml CSTR at a rate of 374 g/hr together with 0.54 g/hr HCl and 120 g/hr ionic liquid and reacted at 10° C. and 100 psi. The volumetric mass balance on the products showed that one kg 2-pentene reacted with 1.56 kg iso-pentane to yield 0.09 kg iso-butane, 0.30 kg light naphtha (bp: 40-130° C.), 1.98 kg heavy naphtha (bp: 130-175° C.), 0.20 kg jet fuel (bp: 175-260° C.) and essentially no heavier products.

Example 4

A heat balance estimation illustrating the advantage of processing the mixed olefins under partial conversion conditions followed by alkylation with the remaining olefins at regular alkylation conditions was performed. It was assumed in this estimation that the partial conversion was operated at temperatures that do not require refrigeration.

The enthalpy of the reaction for the alkylation of iso-pentane with pentenes was assumed to be 66 KJ/mole olefin converted for all types of pentenes (1-pentene, 2-pentenes or iso-pentenes). Under regular refrigerated alkylation conditions this translates to a heat of reaction of 943 KJ/kg olefin. For a refrigerated alkylation reaction, all of this heat of reaction would have to be removed through refrigeration.

If part of the olefins were converted under partial olefin conversion at non refrigerated conditions, this would unload the refrigeration requirements accordingly. Partially converting the olefins under non refrigerated conditions will have much less negative effect on the heavier products formed than if the alkylate naphtha were formed under alkylation conditions with the unconverted mixed olefin feedstock. Thus if half of the olefins were converted under non-refrigerated partial conversion conditions the reaction heat that had to be removed by refrigeration would be lowered to 472 KJ/mole.

In addition, since the products of partial olefin conversion are less sensitive to the iso-alkane/olefin ratio than alkylation, the fractionation delivering the I/O to the partial olefin conversion step could be designed for only half the iso-pentane recycle flow giving substantial savings in the fractionation section as well.

Example 5

Pure iso-butane (301 g/hr) was mixed with a mixed refinery FCC C4 stream at 139 g/hr. The mixed refinery FCC C4 stream had the following composition: 21 wt % 2-butene, 12 % 1-butene, 11% iso-butene, 0.5% propene, 39% iso-butane, 11% n-butane, 1.5% propane, and 4% C5+. The mixture was processed (partially converted) at 10° C. and 50 psi with 0.09 g/hr HCl and 54 g/hr ionic liquid to make a converted olefinic feedstock. The olefin conversion was in the range of 70-91%. Based on mass balance on the products, 1 kg olefin reacted to yield approximately 0.10 kg light naphtha (bp 40-130° C.), 0.06 kg heavy naphtha (bp: 130-200° C.), 0.23 kg jet fuel (bp: 200-290° C.), 0.25 kg diesel fuel (290-360° C.), and 0.36 kg heavy oil (360- ~550° C.). The unconverted olefins from different samples taken during the run were analyzed by GC analysis. The C4 olefin distributions in the samples of the converted olefinic feedstock taken during the run were found to be 9-20 wt % 1-butene, 80-91 wt % 2-butene and 0 wt % iso-butene. For comparison, the C4 olefin distribution in the olefinic feedstock was 27% 1-butene, 48% 2-butene and 25% iso-butene.

Using in-house evaluation tools the alkylate quality that these C4 olefin mixtures would have yielded under typical iso-butane alkylation conditions using N-butyl-pyridinium heptachlorodialuminate and HCl as catalyst was estimated. It was estimated that the untreated olefinic feedstock C4's (27% 1-butene, 48% 2-butene and 25% iso-butene), when processed, would have yielded an alkylate with RON/MON=87/88. For comparison, it was estimated that the unconverted butenes in the converted olefinic feedstock (9-20 wt % 1-butene, 80-91 wt % 2-butene and 0 wt % iso-butene) would have yielded an alkylate with RON/MON=91-95/91-94.

I claim:

1. A process for reacting an iso-pentane, comprising:
   a) partially converting an olefinic feedstock comprising at least 15 wt. % iso-pentene to make a converted olefinic feedstock comprising C5 olefins that are predominantly 2-pentene, wherein the iso-pentene is reduced and an amount of 2-pentene is retained;
   b) alkylating the iso-pentane with the converted olefinic feedstock to make a naphtha and a middle distillate; wherein the partially converting and alkylating are done in the presence of one or more ionic liquid catalysts comprising a hydrocarbyl substituted pyridinium chloroaluminate, a hydrocarbyl substituted imidazolium chloroaluminate, or a mixture thereof.

2. The process of claim 1, wherein the olefinic feedstock comes from a FCC unit or a coker unit.

3. The process of claim 1, wherein the C5 olefins in the converted olefinic feedstock are at least 90 wt % 2-pentene.

4. The process of claim 1, wherein a formation of iso-butane during the alkylating is less than 10 wt % of the amount of olefins in the converted olefinic feedstock.

5. The process of claim 1, wherein the ionic liquid catalyst is mixed with a hydrogen halide or an alkyl halide.

6. The process of claim 1, wherein the one or more ionic liquid catalysts are the same during the converting and alkylating.

7. The process of claim 1, wherein the one or more ionic liquid catalysts comprise a butyl-pyridinium chloroaluminate.

8. The process of claim 1, wherein a process for partially converting is different from olefin isomerization.

9. The process of claim 1, where the partially converting is done at non-refrigerated conditions.

10. The process of claim 1, wherein the middle distillate comprises a jet fuel.

* * * * *